(12) United States Patent
Noel

(10) Patent No.: US 10,716,597 B2
(45) Date of Patent: Jul. 21, 2020

(54) FLAT FLEXIBLE TEXTILE LONGILINE ELEMENT COMPRISING A DEVICE FOR IDENTIFYING ITS OPPOSED A AND B SIDES

(71) Applicant: COUSIN BIOTECH, Wervicq Sud (FR)

(72) Inventor: Stephane Noel, Hantay (FR)

(73) Assignee: COUSIN BIOTECH, Wervicq Sud (FR)

( * ) Notice: Subject to any disclaimer, the term of this patent is extended or adjusted under 35 U.S.C. 154(b) by 0 days.

(21) Appl. No.: 16/185,131

(22) Filed: Nov. 9, 2018

(65) Prior Publication Data

US 2019/0142476 A1    May 16, 2019

(30) Foreign Application Priority Data

Nov. 10, 2017 (FR) ...................................... 17 60600

(51) Int. Cl.
| | |
|---|---|
| *A61B 17/70* | (2006.01) |
| *D04C 1/12* | (2006.01) |
| *A61B 90/92* | (2016.01) |
| *A61B 90/90* | (2016.01) |
| *A61B 17/84* | (2006.01) |

(52) U.S. Cl.
CPC ........ *A61B 17/7053* (2013.01); *A61B 17/842* (2013.01); *A61B 90/90* (2016.02); *A61B 90/92* (2016.02); *D04C 1/12* (2013.01); *D10B 2509/00* (2013.01)

(58) Field of Classification Search
CPC ... A61B 17/7053; A61B 17/842; A61B 90/90; A61B 90/92; D04C 1/12; D10B 2509/00

USPC .................................................... 606/263, 74
See application file for complete search history.

(56) References Cited

U.S. PATENT DOCUMENTS

| | | | | |
|---|---|---|---|---|
| 4,610,688 | A * | 9/1986 | Silvestrini | A61F 2/06 623/1.53 |
| 4,792,336 | A * | 12/1988 | Hlavacek | A61F 2/06 623/13.18 |
| 10,167,582 | B1 * | 1/2019 | Pilgeram | D04C 3/48 |
| 10,323,342 | B1 * | 6/2019 | Callison | A61B 17/06166 |

(Continued)

FOREIGN PATENT DOCUMENTS

| | | |
|---|---|---|
| EP | 0554653 A2 | 8/1993 |
| WO | 2016/154550 A1 | 9/2016 |

*Primary Examiner* — Pedro Philogene
*Assistant Examiner* — David C Comstock
(74) *Attorney, Agent, or Firm* — Workman Nydegger; Matthew D. Todd

(57) ABSTRACT

An implantable device (1) comprising a flat and flexible longilinear textile element (3) having a first face A (15) and a second face B (16) and first and second free ends (11,13) as well as an identification device (20) configured to identify, when said longilinear element (3) forms at least one loop portion (5) delimiting an internal volume Vi, a first position in which the second internal face B (16) is oriented facing the internal volume Vi in said loop portion (5), the second internal face B (16) of the first free end (11) being directly facing the second internal face B (16) of the second free end (13); a second position in which the first external face A (15) is oriented facing the internal volume Vi according to at least one part of the loop portion (5), the second internal face B (16) of the first free end (11) being directly facing the first external face A (15) of the second free end (13).

12 Claims, 3 Drawing Sheets

(56) References Cited

U.S. PATENT DOCUMENTS

| | | |
|---|---|---|
| 2012/0059419 A1 | 3/2012 | Alamin |
| 2014/0172096 A1* | 6/2014 | Koob ........................ A61F 2/08 623/13.19 |
| 2016/0168769 A1* | 6/2016 | McDonnell .............. D04C 1/06 87/9 |

* cited by examiner

FLAT FLEXIBLE TEXTILE LONGILINE ELEMENT COMPRISING A DEVICE FOR IDENTIFYING ITS OPPOSED A AND B SIDES

BACKGROUND OF THE INVENTION

The present invention relates to an implantable device comprising a flat flexible textile longilinear element and an identification device for determining whether the longilinear element, when passed around an osseous portion or another body, is twisted.

The flat textile longilinear elements can be implanted singly, or in combination with another implantable device with which they cooperate, for example to ensure the link between an osseous body and a distraction rod. Such longilinear textile elements offer good mechanical resistance due to their construction using several threads.

The implanted flat longilinear element can form one or more loops. Now, it is important that said longilinear element is not twisted on its implantation trajectory. In fact, the twisted zone can form a zone having an abrasive effect on the surrounding tissue. Also, mechanical performances offered by the longilinear element are not optimized in a poor implantation position. It is often not possible for the practitioner to verify the position adopted by the flat longilinear element as the latter has passed through tissues in a blind manner using surgical tools. Once the flat longilinear element is implanted, only its ends are visible and prehensible so that they are joined together and/or to a device so they can be joined. The flat longilinear element is also generally tensed, which tension when exerted on a twisted portion can amplify the shearing effect on the tissue. Also, one of the advantages of a flat textile longilinear element compared to a circular longilinear element is that its plane faces naturally generate no shearing effect.

The subject matter of EP 0 554 653 A2 is a circular implantable braid comprising threads of colour. The function of these threads of colour is to distinguish one braid from another, the threads of colour being associated with performances determined for each of the braids. Also, EP 0 554 653 A2 does not try to determine the twisted position of a braid, which is not possible due to the circular form of the braid.

AIM AND SUMMARY OF THE INVENTION

The aim of the present invention is to propose an implantable device comprising a flat flexible textile longilinear element for determining, when it forms a loop portion, if it is twisted to avoid any risk of whether tissue and/or bones around which it is arranged.

The aim of the present invention is to propose an implantable device simple to use, and simple to manufacture, without diminishing its mechanical resistance, especially to breaking.

The present invention eliminates the above problems in that its object is an implantable device comprising a flat flexible textile longilinear element having a first face A and a second face B opposite the first face A, as well as first and second free ends. Advantageously, the implantable device comprises an identification device configured to identify, when said longilinear element forms at least one loop portion, in particular by passing around at least one osseous part, said loop portion delimiting an internal volume Vi, a first position of the loop portion in which the second internal face B is oriented facing the internal volume Vi in said loop portion, the second internal face B of the first free end being directly facing the second internal face B of the second free end;

a second position of the loop portion in which the first external face A is oriented facing the internal volume Vi according to at least one part of the loop portion, the second internal face B of the first free end being directly facing the first external face A of the second free end.

Advantageously, if the longilinear element is twisted in said loop portion, it is possible by means of the identification device by superposing the two free ends, in the substantially rectilinear extension of the loop portion, to verify the orientation of the first external face A relative to the second internal face B, and to do this without verifying the arrangement of the loop portion directly. Because of the identification device, analysis of the direction of the plane opposite faces A and B of the longilinear element identifies whether the longilinear element is twisted in the loop portion.

It is in fact not possible in the prior art to differentiate the two flat opposite faces of an implantable longilinear textile element.

In the present invention, if the longilinear element forming at least one loop portion is not twisted, the first external face A substantially retains the same orientation according to the trajectory of said longilinear element, at least in said portion. The first external face A therefore remains oriented to the exterior of the internal volume Vi formed by said at least one loop portion. In parallel, the second internal face B also retains the same orientation according to the trajectory of the longilinear element, at least in said portion. The second internal face B therefore remains oriented towards the interior of the internal volume Vi.

By contrast, if the longilinear element forming at least one loop portion is twisted in said portion, the first external face A, and therefore also the second internal face B, are reversed in said portion. The first external face A is oriented towards the interior of said at least one loop portion, in particular oriented facing the internal volume Vi. The second internal face B is as such oriented towards the exterior of the internal volume Vi of the loop portion. The identification device according to the invention identifies whether the seconds internal faces B are not oriented directly facing each other, in the region of the free ends of the longilinear element, at output of the loop portion, and therefore deduces whether the longilinear element is twisted in the loop portion.

The longilinear textile element is flexible as it can be rolled up, and therefore completely envelop a portion of an osseous body or a muscle or even another organ.

The longilinear element by definition has a length clearly larger than its width, for example a length of the order of 10 cm to 50 cm.

Preferably, the longilinear element has a width I greater than 0 mm and less than or equal to 30 mm, more preferably less than or equal to 20 mm, especially greater than or equal to 5 mm.

Preferably, the longilinear element has a thickness of over 0 mm and less than or equal to 10 mm, more preferably less than or equal to 8 mm, preferably less than or equal to 5 mm.

The longilinear textile element is obtained by the implementation of threads and/or auxiliary longilinear elements (for example one or more braids, ribbons, . . . ) on a textile machine (especially a knitting, weaving (of slight width), or braiding machine).

The longilinear textile element can comprise a polymer coating, even though it preferably does not comprise one.

The identification device is configured so that a user can differentiate the first face A as opposed to the second face B. This identification device can accordingly comprise visual identification means and/or tactile identification means. For example, one of the two faces A and B can comprise elements in relief while the other face is substantially smooth to the touch.

For example, one of the two faces A and B can comprise a first coloured pattern while the other face comprises a second pattern, different to the first pattern, or comprises none.

The longilinear textile element comprises a multifilament thread or multifilament threads and/or a monofilament thread or monofilament threads and/or a spun yarn thread or spun yarn threads, preferably selected in one material or synthetic polymer materials, resorbable or not, more preferably the polymer material or said polymer materials is/are selected from: polyesters such as polyethylene terephthalate; polyamides such as PA 6, PA 6-6, PA 4-6, PA 11 or 12; polyolefins such as polypropylene, and polyethylene; preferably polypropylene; lactic acid polymers, and especially polylactic acid of form L or D or their mixture (PLLA, PLA, PDLA); or their mixture.

Preferably, the monofilament thread or the monofilament threads have an external diameter greater than 0 mm, and less than or equal to 5 mm, more preferably less than or equal to 2 mm, preferably less than or equal to 1 mm, especially less than or equal to 0.5 mm.

Preferably, the monofilament thread or the multifilament threads has/have a titre greater than 50 dtex, especially less than or equal to 2000 dtex.

The longilinear element can be hollow, in this case comprising two superposed textile layers, or not be hollow and be formed in this case from a single textile layer.

The longilinear textile element can be flat and hollow at output of the textile machine, for example at output from a minimal width weaving machine, or at output from a braiding machine, or again can be in the form of a tube at output from a braiding or knitting machine. In the latter case the longilinear textile element undergoes thermal processing so as to flatten it and give it flat and opposite faces A and B.

When the textile element comprises two textile layers superposed, the first and second faces A and B correspond to the external faces of the two textile layers. The internal faces of the two textile layers are oriented facing each other and terminate in the internal volume of said hollow longilinear element.

In a variant, the identification device is of unitary textile construction with the longilinear textile element, in particular knitted, braided or woven construction, unitary with the longilinear knitted, braided or woven textile element respectively.

Advantageously, the identification device is arranged in the longilinear element during manufacture on a textile machine. This arrangement facilitates manufacture of the longilinear element and ensures good reproducibility in the arrangement of the identification device over the length of the longilinear element.

The identification device also contributes to the mechanical resistance of the longilinear textile element.

The identification device is preferably selected from: one or more multifilament threads and/or monofilament and/or threads spun yarn, one or more ribbons, one or more braids, the or which is/are optionally coloured, in particular in a colour or colours different to the colour or colours used in the rest of the longilinear element.

The arrangement for example of a coloured thread braided with a set of other non-coloured threads also braided in a braid is not enough to form an identification device according to the invention. In fact, arranging the identification device, and therefore the coloured thread, must be determined such that the first external face A can be differentiated from the second internal face B.

In a variant embodiment, the identification device comprises visual and/or tactile identification means of the first external face A and of the second internal face B, said means being braided, knitted or woven during knitting, braiding or weaving of the longilinear textile element.

In a variant, the identification device is arranged on the first external face A and/or on the second internal face B, continuously or discontinuously, over the entire length of the longilinear textile element.

In a variant, the identification device is arranged according to one of the two longitudinal sides of the longilinear element, both on the first external face A and on the second internal face B.

The identification device is arranged according to the first side or the second longitudinal side of the first external face A, and so as to be facing also on the second internal face B, according to the first longitudinal side or the second longitudinal side respectively.

In this case the identification device is arranged according to the right longitudinal half or the left longitudinal half of one of the faces A and B and is not centred on the width of the longilinear element. In fact it would not be possible to distinguish the faces A and B in the latter case.

In a variant, the identification device comprises one or more flexible auxiliary longilinear elements, such as one or more monofilament and/or multifilament threads and/or spun yarn, one or more braids, one or more ribbons, or their mixture.

In a variant, the flat textile longilinear element is a hollow braid.

In a variant, the longilinear textile element is a triaxial braid comprising a first set of at least one braided thread according to an axis L1, a second set of at least one braided thread according to an axis L2, and the identification device, braided according to an axis L3, said axes L1, L2 and L3 being different.

The identification device is braided with the first and second sets of threads.

Preferably, the longilinear element comprises, in particular is constituted by, first and second sets of threads, as well as a third set of at least one thread, braided according to the axis L3. More preferably the third set of at least one thread is arranged on the first external face A, and optionally on the second internal face B and the identification device is arranged on the second internal face B, and in particular the identification device is not arranged on the first external face A.

The identification device can be formed by one or more threads, such as defined in the present text, optionally coloured in one or more colours different to the colour or colours of the threads of the first, second, and optionally third, sets of threads.

Advantageously, it is possible to preferably have one or more threads determined according to only one of the two faces A and B.

The longilinear element has a central longitudinal axis A1 and a transversal axis T, substantially perpendicular to the axis A1.

The central longitudinal axis A1 passes at the centre of the faces A and B.

The axes L1 and L2 respectively form angles +α1 and −α2 with the axis A1 (with |α1|≠|α2| or |α1|=|α2|), which angles |α1| and |α2| are greater than 0° and less than 180°, especially less than 90°, in particular less than 50°, especially of the order of 45° at +/−5°.

Preferably, the axis A1 is substantially parallel to the axis L3.

In a variant embodiment, the longilinear textile element comprises superposed first and second layers textile, the external face of the first layer textile being formed from the first external face A, and the external face of the second layer textile being formed from the second internal face B.

The internal faces of the first layer textile and of the second layer textile are facing each other, and terminate in the internal volume delimited between said first and second layers.

The first and second layers textile superposed are of unitary textile construction, obtained in particular by braiding a hollow braid.

In an embodiment, the first layer textile comprises the identification device, especially terminating on the external face of said first layer, and optionally on the internal face of the latter.

When the longilinear textile element is a hollow triaxial braid, the identification device is arranged according to the axis L3 on the first braided layer, in particular without being on the second braided layer.

In an embodiment, the first braided layer is obtained by braiding the first and second sets of threads with the identification device, and optionally the third set of threads. Preferably, the second braided layer is obtained by braiding the first, second and third sets of threads.

In a variant, the flat textile longilinear element has a longitudinal axis A1, and the identification device has a substantially rectilinear trajectory according to the axis L3, the axis L3 and the longitudinal axis A1 being parallel.

In a variant, the identification device comprises proeminent loops, arranged continuously or discontinuously, on the first external face A and/or the second external face B, preferably said loops are constituted by one multifilament thread or by several multifilament threads.

Preferably, the tension applied during textile execution, especially by braiding, and/or elongation at break of the multifilament thread or multifilament threads forming the identification device is/are different, especially greater, than the tension applied and/or elongation at break of the other thread or other threads forming the longilinear textile element for creating excesses of lengths of threads forming loops projecting from the face A and/or the face B, preferably according to a single one of the two faces A and B.

BRIEF DESCRIPTION OF THE DRAWINGS

The invention and its advantages will be better understood from the detailed description of particular embodiments taken by way of non-limiting examples and illustrated by the appended drawings, in which.

DETAILED DESCRIPTION OF THE INVENTION

Figure 1:
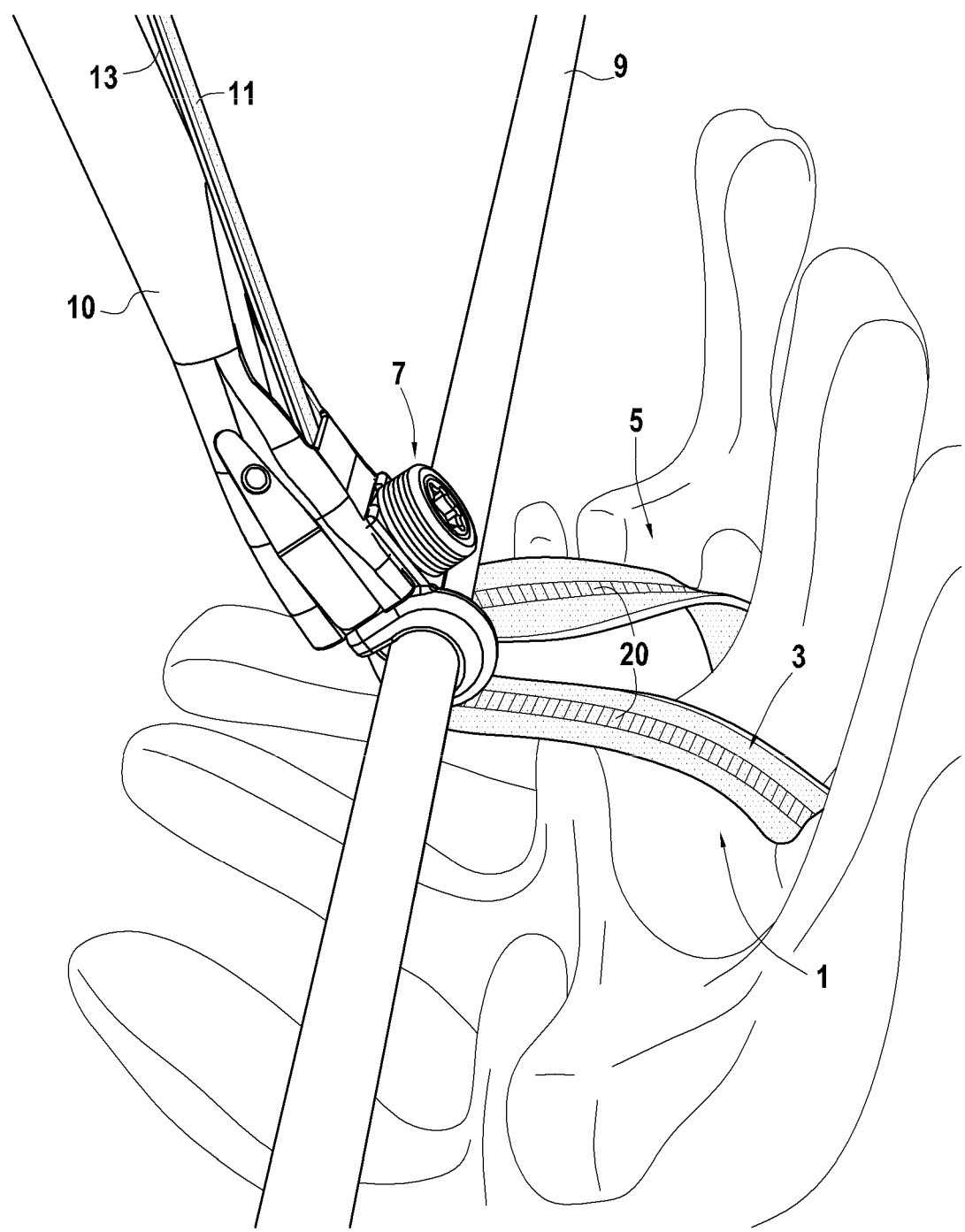
FIG. 1 is a schematic representation of a first example of an implantable device according to the invention arranged on a less osseous portion in the first position.

FIG. 1 illustrates the arrangement of a first example of an implantable device 1 according to the invention in which the flat and flexible textile longilinear element 3 is arranged around at least one portion of a vertebral body by forming a loop portion 5 in the first position. The longilinear textile element 3, in this exact example, cooperates with a connector 7 and an implantable rod 9, but it can be used alone or in combination with other implants. Also, the longilinear element 3 can form a loop 5 around another type of body, osseous or not, for example around a muscle or an organ. The free ends 11 and 13 of the longilinear element 3, after the latter has been tensed by way of the tensioning device 10 shown partially, are joined together by means of the connector 7.

The flat flexible textile longilinear element 3, shown in FIGS. 1 and 2A to 2C, has a first face A 15 and a second face B 16 opposite the first face A 15, and first and second free ends 11,13. The longilinear textile element 3 has a central longitudinal axis A1, and a transversal axis T.

The implantable device 1 comprises an identification device 20 configured to identify, when said longilinear element 3 forms at least one loop 5, in particular by passing around at least one osseous portion, said loop 5 delimiting an internal volume Vi,
  a first position of the loop 5 in which the second internal face B 16 is oriented facing the internal volume Vi in said loop 5, the second internal face B 16 of the first free end 11 being directly facing the second internal face B 16 of the second free end 13; and
  a second position of the loop 5 in which the first external face A 15 is oriented facing the internal volume Vi according to at least one portion of the loop 5, the second internal face B 16 of the first free end 11 being directly facing the first external face A 15 of the second free end 13.

The identification device 20 is of unitary textile construction with the longilinear textile element 3, in particular of unitary braided construction with the braided longilinear textile element 3.

The identification device 20 comprises at least one visual and/or tactile identification means 22 (see FIG. 2C), in this exact visual example, of the first external face A 15, said at least one identification means 22 being braided during braiding of the longilinear textile element 3.

The identification device 20 is arranged on the first external face A 15, continuously or discontinuously, in this exact example continuously, over the entire length of the longilinear textile element 3.

The flat longilinear textile element 3 is a hollow triaxial braid 25 obtained by braiding a first set 30 of threads according to an axis L1, a second set 35 of threads according to an axis L2, a third set 45 of threads according to the axis L3, and of the identification device 20 according to the axis L3, said axes L1, L2 and L3 being different. The assembly mode of the different sets of threads 30,35,45 and identification device 20 is shown schematically in FIG. 2C.

The identification device 20 comprises in particular a plurality of threads 40, especially multifilament, distinct visually and/or tactilely, of threads of the first, second and third sets 30,35,45. In this exact example, the threads 40 are in a colour, blue for example, different to the colour or colours of the threads of the first, second and third sets 30,35,45, the latter especially being white.

The identification device 20 has a substantially rectilinear trajectory according to the axis L3, the axis L3 and the central longitudinal axis A1 being parallel.

Figure 3:
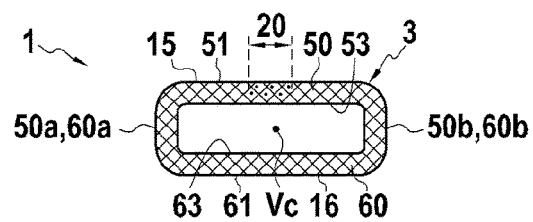
FIG. 3 is a schematic representation according to the cutting plane III-III shown in FIG. 2A of the flat textile longilinear element of the first example of an implantable device.

The longilinear textile element 3 comprises two braided layers 50,60 attached by their longitudinal sides 50a,60a; 50b,60b during braiding and delimiting a hollow internal volume Vc (FIG. 3). The first braided layer 50 comprises an external face 51 forming the first external face A 15 and an internal face 53 terminating in the internal volume Vc. The second braided layer 60 comprises an external face 61 forming the second internal face B 16 and an internal face 63 also terminating in the internal volume Vc. The internal faces 53 and 63 of the first and second layers 50,60 are facing each other.

Figure 2A:
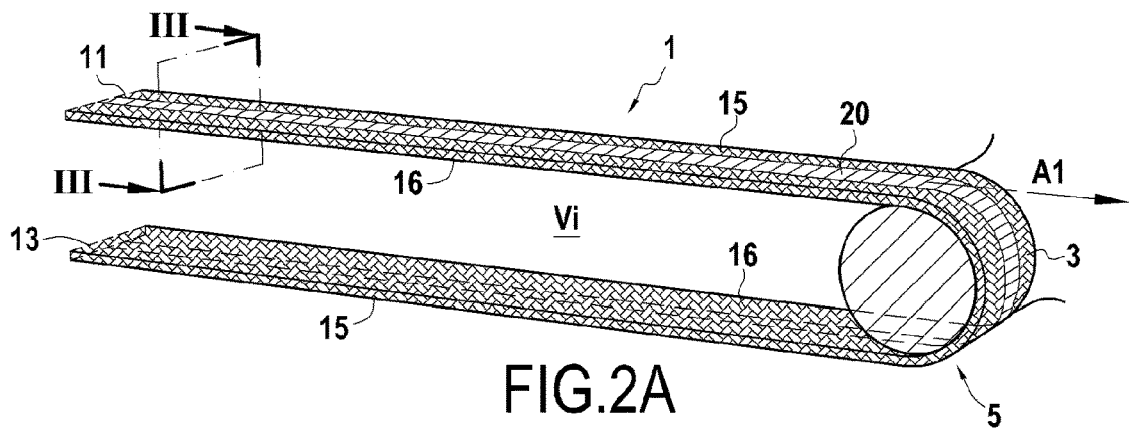
FIG. 2A is a schematic representation of the first example of an implantable device alone in the first position.
Figure 2B:
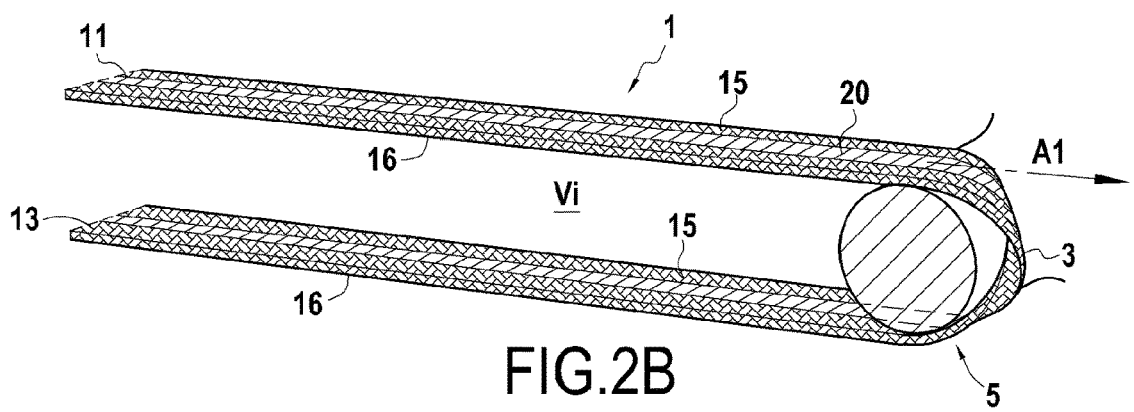
FIG. 2B is a schematic representation of the first example of an implantable device alone in the second position.
Figure 2C:
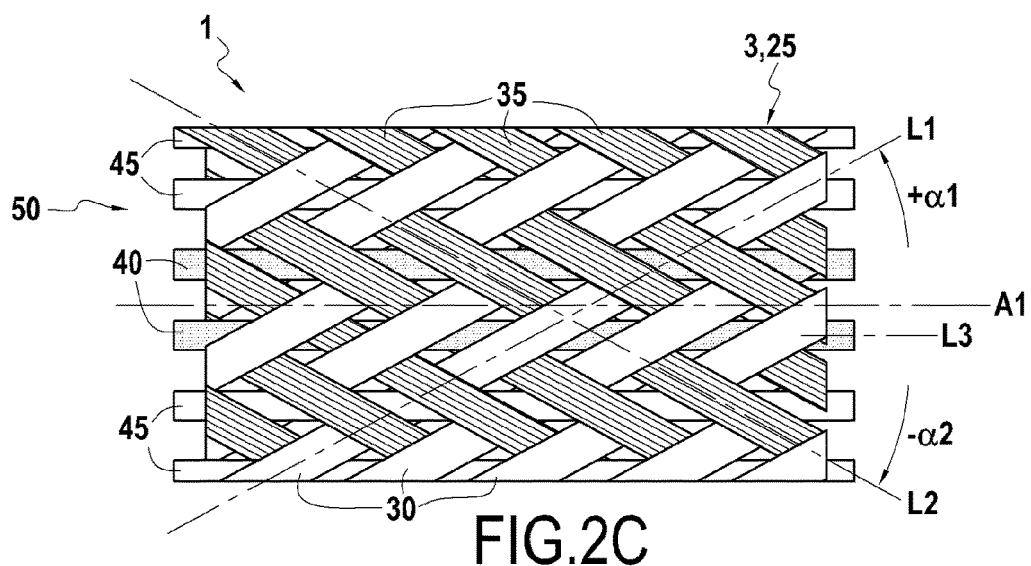
FIG. 2C is a schematic representation of the braiding mode of the first layer of the flat textile longilinear element of the first example of an implantable device.

Only part of the first braided layer 50 of the triaxial braid 25 is shown in FIG. 2C, said layer 50 comprising the identification device 20 which will be visible both on its external face 51, and therefore the first external face A 15, and on its internal face 53. The first layer 50 comprises threads of the third set of threads 45 such as shown in FIG. 2C. The first layer 50 also may not comprise threads of the third set of threads 45, and in this case the identification device 20 comprises more threads to replace said third set of threads 45.

The second layer 60 of the triaxial braid 25 comprises in this exact example, the three sets of threads 30,35,45 braided according to the axes L1, L2 and L3 and comprises no identification device 20.

In this exact example al is of the order of +30° and α2 is of the order of −30°. In another preferred variant, not shown, al is of the order of +45° and α2 is of the order of −45°.

In a preferred example, the first set 30 comprises 24 threads, especially white in colour, each thread being formed by six multifilament threads of 138 dtex each (which are arranged parallel or slightly twisted), especially made of polyethylene terephthalate (PET), or a total of 19 872 dtex (=24*(6*138)). The second set 35 comprises 24 threads, especially white in colour, each thread being formed by six multifilament threads of 138 dtex each (which are arranged parallel or slightly twisted), or a total of 19 872 dtex (=24*(6*138)). The third set 45 comprises twelve threads, each thread being formed by six multifilament threads of 138 dtex each (which are arranged parallel or slightly twisted), or a total of 9 936 dtex (=12*(6*138) dtex), in particular made of PET, these threads being arranged on the second internal face B 16. The identification device 20 comprises twelve threads, each thread being formed by six multifilament threads of 138 dtex each (which are arranged parallel or slightly twisted), in particular made of PET, or a total of 9 936 dtex (=12*(6*138) dtex). These threads are especially mass-dyed, and arranged on the first external face A 15, which in this preferred example includes no threads of the third set of threads 45 on the first layer 50. The threads of the third set of threads 45 are arranged on the second layer 60.

Triaxial braiding of the three sets of threads 30,35,40 and of the identification device is advantageously configured such that the threads forming the identification device are arranged on a single one of the two braided layers for visually and definitely identifying the first external face A of the second internal face B.

When operating, the flat textile longilinear element 3 is arranged around the vertebral body shown in FIG. 1, then its ends 11,13 are combined and superposed in the extension of the loop 5, without being twisted, of course. If the second internal face B 16 of the first free end 11 is directly facing the second internal face B 16 of the second free end 13, the implantable device 1 is in the first position and is therefore not twisted. If on the contrary the second internal face B 16 of the first free end 11 is directly facing the first external face A 15 of the second free end 13, the implantable device 1 is in the second position, and is twisted in the loop portion 5. It is then possible to correct the position of the loop portion 5 and then to control that the longilinear element 3 is now in the first position.

Figure 4A:
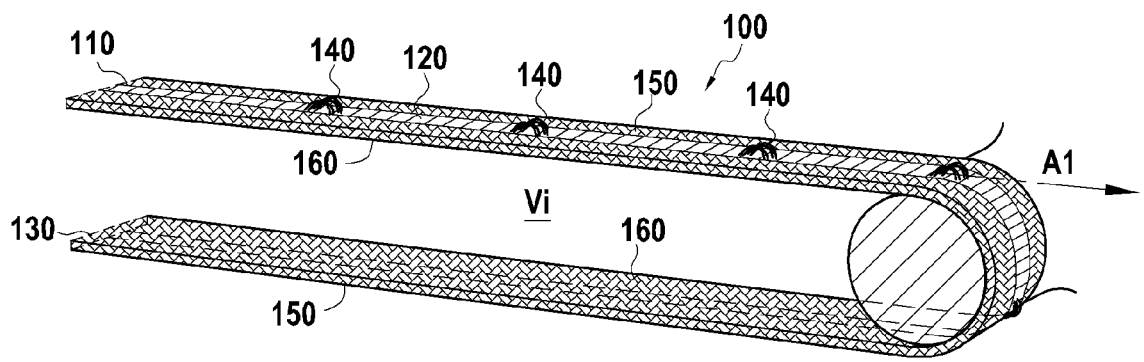
FIG. 4A is a schematic representation of a second example of an implantable device alone in the first position.
Figure 4B:
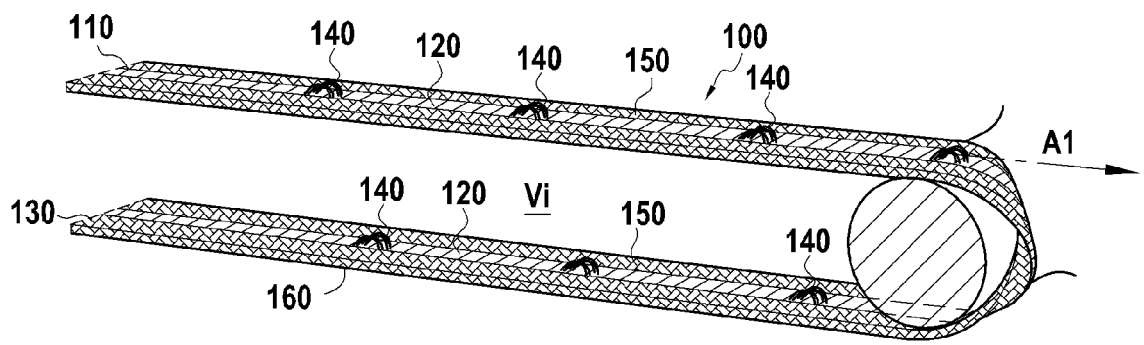
FIG. 4B is a schematic representation of the second example of an implantable device alone in the second position.

The second example of an implantable device 100 shown in FIGS. 4A and 4B differs from the first example of an implantable device 1 by its identification device 110. The identification device 110 is also formed by several braided threads 120 with first, second and third sets of threads to form a triaxial braid 130. The threads 120 forming the identification device 110 however are braided with a tension less than that applied to the threads of the first, second and third sets of threads such that the threads 120 of the identification device 110 form loops 140 at regular intervals. The identification device 120 is therefore visual here but also tactile. The proeminent loops 140 also improve identification of the first external face A 150 compared to the second internal face B 160.

Figure 5A:
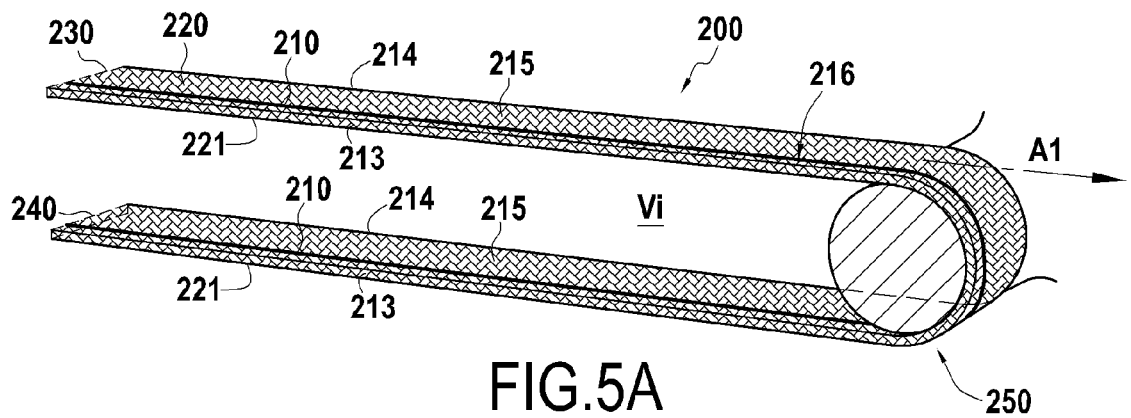
FIG. 5A is a schematic representation of a third example of an implantable device alone in the first position.
Figure 5B:
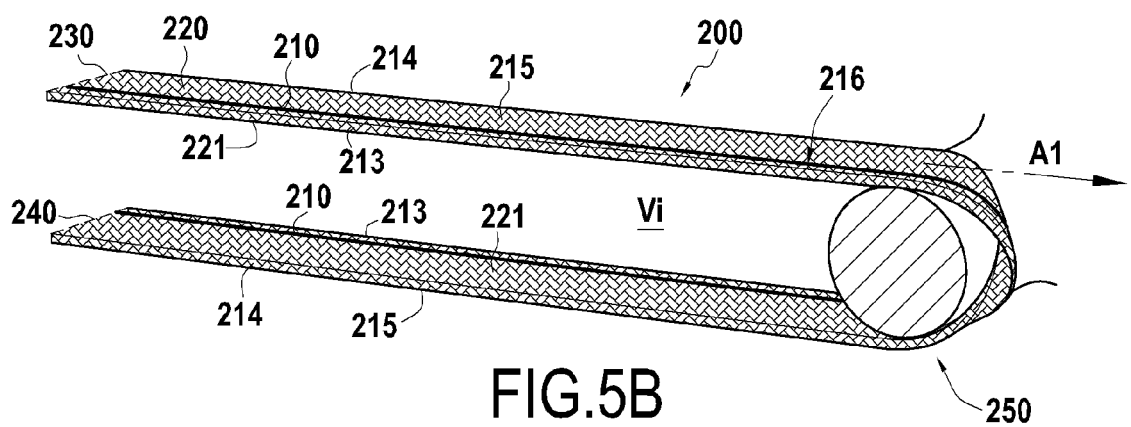
FIG. 5B is a schematic representation of the third example of an implantable device alone in the second position.

The third example of an implantable device 200 shown in FIGS. 5A and 5B comprises an identification device 210 arranged according to one of the first and second longitudinal sides 213,214 of the flat longilinear element 215, in this precise example according to the first longitudinal side 213 on the first external face A 220, and on the second internal face B 221. The flat textile longilinear element 215 is a non-hollow flat braid, comprising a single layer. When the flat longilinear element 215 is in the first position, the identification device 210 is arranged according to the same first longitudinal side 213 in the regions of its free ends 230,240. By contrast, if the longilinear element 215 is twisted in the loop portion 250, the identification device 210 is visually as if it were arranged according to the second longitudinal side 214 of the longilinear element 215.

The different variants of an implantable devices 1,100,200 according to the invention are easy to execute and of simplified construction. The mechanical resistance of the longilinear element 3,130,215 is preserved since it is preferably of unitary textile construction with the flat textile longilinear element 3,130,215, in particular during braiding.

It is therefore easy to identify by comparing the faces A and B of the longilinear element in the region of the two free ends if the latter is twisted in the loop portion upstream, and therefore to correct the arrangement of the longilinear element until it is in the first position.

The invention claimed is:

1. An implantable device comprising a hollow flat flexible longilinear textile element having a first external face A and a second external face B opposite the first external face A, as well as first and second free ends, and an internal volume wherein the implantable device comprises an identification device configured to identify, when said longilinear element forms at least one loop portion, said loop portion delimiting an internal volume Vi,
- a first position of the loop portion in which the second external face B is oriented facing the internal volume Vi in said loop portion, the second external face B of the first free end being directly facing the second external face B of the second free end;
- a second position of the loop portion in which the first external face A is oriented facing the internal volume Vi according to at least one part of the loop portion, the second external face B of the first free end being directly facing the first external face A of the second free end,
- wherein the identification device is arranged at least on the first external face A, continuously or discontinuously, over the entire length of the longilinear textile element, and
- wherein the longilinear textile element comprises a first textile layer having the first external face A and a first internal face, and a second textile layer having the second external face B and a second internal face, said first and second textile layers are superposed, and
- the first and second internal faces terminate in the internal volume.

2. The implantable device according to claim 1, wherein the identification device is of unitary textile construction with the longilinear textile element.

3. The implantable device according to claim 2, wherein the identification device is of unitary textile construction with the longilinear textile element by knitted, braided or woven construction.

4. The implantable device according to claim 1, wherein the identification device comprises at least one visual and/or tactile identification means of the first external face A and of the second internal external face B, said means being braided, knitted or woven during knitting, braiding or weaving of the longilinear textile element.

5. The implantable device according to claim 1, wherein the identification device is arranged on the first external face A and/or on the second external face B, continuously or discontinuously, over the entire length of the longilinear textile element.

6. The implantable device according to claim 5, wherein the identification device is arranged according to one of the two longitudinal sides of the longilinear element, both on the first external face A and on the second external face B.

7. The implantable device according to any one of claim 1, wherein the identification device comprises a flexible auxiliary longilinear element, such as one or more monofilament or multifilament threads, one or more braids, one or more ribbons.

8. The implantable device according to claim 1, wherein the flat textile longilinear element is a hollow braid.

9. The implantable device according to claim 1, wherein the longilinear textile element is a triaxial braid comprising a first set of at least one braided thread according to an axis L1, a second set of at least one braided thread according to an axis L2, and the identification device is braided according to an axis L3, said axes L1, L2 and L3 being different.

10. The implantable device according to claim 1, wherein the flat textile longilinear element has a longitudinal axis A1, and the identification device has a substantially rectilinear trajectory according to an axis L3, the axis L3 and the longitudinal axis A1 being parallel.

11. The implantable device according to claim 1, wherein the identification device comprises proeminent loops, arranged continuously or discontinuously, on the first external face A and/or the second external face B.

12. The implantable device according to claim 1, wherein when said longilinear element forms at least one loop portion, the loop portion is formed by passing the longilinear element around at least one osseous part.

* * * * *